US00PP10944P

United States Patent [19]

Fuess

[11] Patent Number: Plant 10,944

[45] Date of Patent: Jun. 8, 1999

[54] CHRYSANTHEMUM PLANT NAMED 'EMPIRE CALICO'

[76] Inventor: Janet S. Fuess, 22 Country Club Dr., New York Mills, N.Y. 13417

[21] Appl. No.: 08/968,245

[22] Filed: Nov. 12, 1997

[51] Int. Cl.[6] ..... A01H 5/00

[52] U.S. Cl. ..... Plt./82.2

[58] Field of Search ..... Plt./82.2

*Primary Examiner*—Howard J. Locker

*Attorney, Agent, or Firm*—Foley & Lardner

[57] ABSTRACT

A new and distinct cultivar of Chrysanthemum plant named 'Empire Calico', characterized by the combined features of bright yellow ray floret color, daisy capitulum form with many disc florets and a distinct red-purple disc center, capitulum diameter 2.75–3.0 cm, 7 week flower response in light/shade programs, semi-upright growth habit, natural season flowering date of September 20, and adaptability to greenhouse or garden cultures.

1 Drawing Sheet

The present invention comprises a new and distinct cultivar of *Dendranthema grandiflora*, referred to by the cultivar name 'Empire Calico'.

'Empire Calico' is a product of a planned breeding program which had the objective of creating new Chrysanthemum cultivars with freely branching and compact cushion habits, early flower response, and durable, uniform performance with minimal color fading under outdoor conditions. Such traits in combination were not present in previously available commercial cultivars.

'Empire Calico' was originated from a hybridization made by the inventor in a controlled breeding program in New Hartford, N.Y. in October 1992. The female parent of 'Empire Calico' was 'Empire Ventura', disclosed in U.S. Plant Pat. No. 9,384, a cultivar of daisy type and yellow-orange ray florets. The male parent of 'Empire Calico' was E89-4, an unnamed seedling identified as a bright yellow daisy type mum.

'Empire Calico' was discovered and selected as one flowering plant within the progeny of the stated parentage by Janet S. Fuess in September 1993, in a controlled environment in New Hartford, N.Y.

The first act of asexual reproduction of 'Empire Calico' was accomplished when vegetative cuttings were taken by inventor Janet Fuess from the initial selection in October 1993 in a controlled environment in New Hartford, N.Y. Horticultural examination of selected units initiated in September 1994 has demonstrated that the combination of characteristics as herein disclosed for 'Empire Calico' are firmly fixed and are retained through successive generations of asexual reproduction.

'Empire Calico' has not been observed under all possible environmental conditions. The phenoytpe may vary significantly with variations in environment such as temperature, light intensity and day length, without, however, any variation in genotype.

The following observations, measurements and comparisons describe plants grown in New Hartford, N.Y. under natural outdoor conditions which approximate those generally used in commercial practice.

The following traits have been repeatedly observed and are determined to be basic characteristics of 'Empire Calico', which, in combination, distinguish this Chrysanthemum as a new and distinct cultivar:

1. Daisy capitulum type, with three rows of ray florets.
2. Bright yellow ray floret color.
3. Distinct red-purple center on disc, varying in size from 2.5 mm to 5 mm in mature flowers.
4. Flowers have an average of 85 ray florets and 226 disc florets.

5. Diameter across face of capitulm is 2.75–3.0 cm when fully open.
6. Fully expanded ray florets are 1.0–1.25 cm long and approximately 5 mm wide.
7. Natural season flowering date of September 20.
8. A flowering response of 7 weeks in a controlled light/shade program.
9. Semi-upright growth habit, with 7–9 branches per plant after pinch.
10. Adaptability to greenhouse and garden cultures.

Of the many commercial cultivars known to the present inventor, the most similar in comparison to 'Empire Calico' is the female parent 'Empire Ventura'. In comparison to 'Empire Ventura', 'Empire Calico' has bright yellow ray florets (compared to yellow-orange ray florets of 'Empire Ventura'), one more row of ray florets, slightly smaller diameter across face, a distinct red-purple center on disc, and slightly earlier natural season flowering date. The semi-upright habit, 7 week light/shade flower response and overall height in 8" pot are similar to those same characteristics of 'Empire Ventura'.

The accompanying color photographic drawing shows typical inflorescence and foliage characteristics of 'Empire Calico', with the colors being as nearly true as possible with illustrations of this type.

In the following description, color references are made to The Royal Horticultural Society (R.H.S.) Color Chart. The color values were determined between 10:00 a.m. and 1:00 p.m. on Sep. 24, 1996 under 4,000 footcandles of light intensity at New Hartford, N.Y.

Classification:

*Botanical.*—*Dendranthema grandiflora*.cv 'Empire Calico'.

*Commercial.*—Daisy garden mum.

Inflorescence

Capitulm:

*Form.*—Flat.

*Type.*—Daisy.

*Diameter across face.*—2.75–3.0 cm.

Corolla of ray florets:

*Color (general tonality from a distance of three meters).*—Yellow.

*Color (upper surface).*—12A.

*Color (lower surface).*—12B.

Disc Florets: None.

*Color (mature).*—15B, mature eye or center 187A.

*Color* (*immature*).—6A, eye 187A.

Reproductive organs:

*Androecium.*—Present disc florets only; moderate pollen.

*Gynoecium.*—Present on both ray and disc florets; style on ray florets are 4 mm and bifurcated; style on disc florets are 3 mm, bifurcated and enclosed in another ring.

Plant

General Apperance:

*Height.*—25–30 cm when grown in an 8 inch pot under natural day length (no growth regulators).

Foliage:

*Color* (*top surface*).—147A.

*Color* (*under surface*).—147B.

*Shape.*—Deeply lobed, with minute point at end of lobe.

*Size.*—4.0–4.5 cm long, 2.75–3.0 cm wide.

I claim:

1. A new and distinct cultivar of Chrysanthemum plant named 'Empire Calico', as illustrated and described.

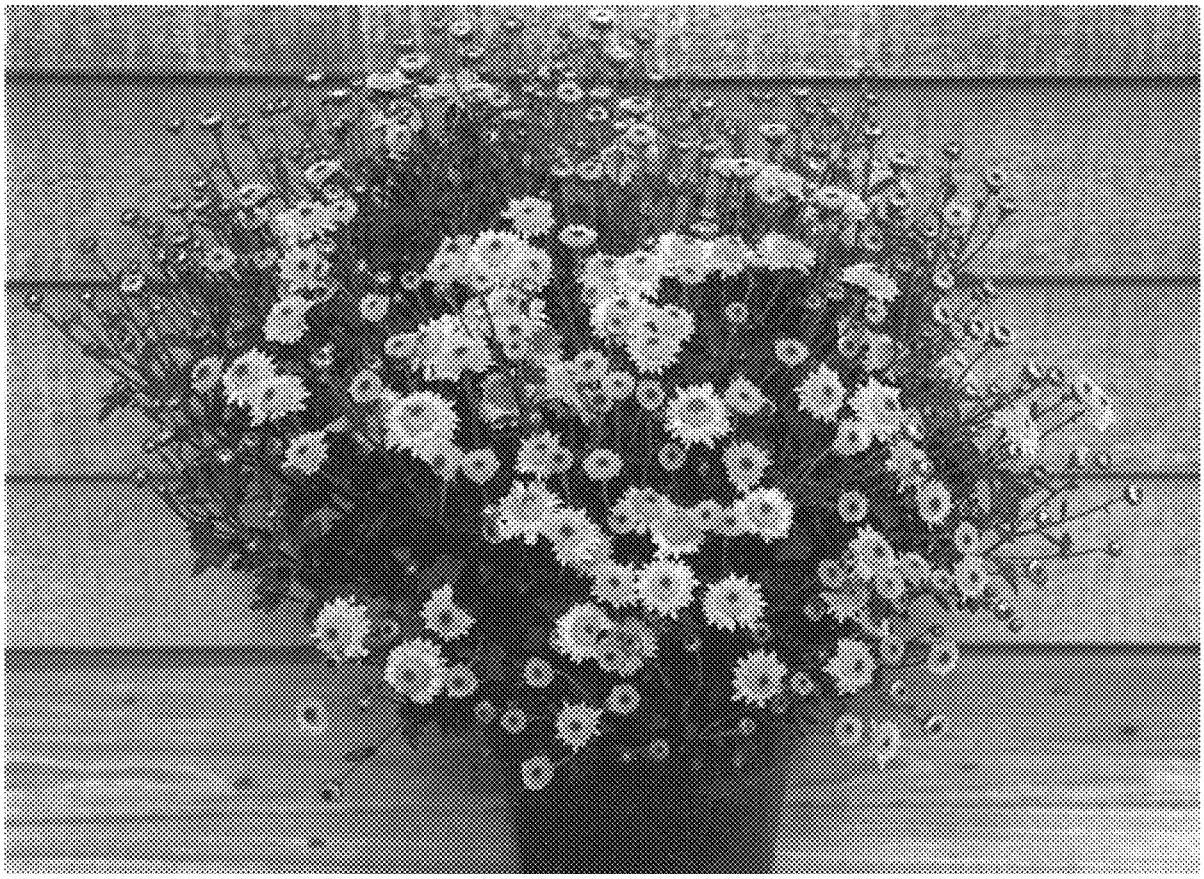

* * * * *